United States Patent [19]
Kuiper et al.

[11] Patent Number: 5,874,215
[45] Date of Patent: Feb. 23, 1999

[54] AMPLIFICATION OF SIMPLE SEQUENCE REPEATS

[75] Inventors: Martin T. R. Kuiper, Bennekom, Netherlands; Marc Zabeau, Gent, Belgium; Picter Vos, Renswoude, Netherlands

[73] Assignee: Keygene N.V., Wagfningen, Netherlands

[21] Appl. No.: 585,888

[22] Filed: Jan. 16, 1996

[30] Foreign Application Priority Data

Jan. 16, 1995 [EP] European Pat. Off. ........... 95400080.8

[51] Int. Cl.⁶ .............. C12Q 1/68; C12P 19/34; C07H 21/02; C07H 21/04
[52] U.S. Cl. ............ 435/6; 435/91.2; 536/23.1; 536/24.3
[58] Field of Search .............. 435/6; 536/24.3, 536/23.1; 935/76, 77, 78

[56] References Cited

U.S. PATENT DOCUMENTS 5,576,180 11/1996 Melanon et al. ........................ 435/6

FOREIGN PATENT DOCUMENTS

| | | |
|---|---|---|
| 534 858 | 3/1993 | European Pat. Off. . |
| 552 545 | 7/1993 | European Pat. Off. . |
| WO93/16196 | 8/1993 | WIPO . |
| WO93/16197 | 8/1993 | WIPO . |
| 94/17203 | 8/1994 | WIPO . |
| 94/28175 | 12/1994 | WIPO . |
| 96/17082 | 6/1996 | WIPO . |

OTHER PUBLICATIONS

Zietkiewicz et al., Genomics 20 :176–183 (1994).
Baron et al., Nucleic Acids Research 20(14) : 3665–3669 (1992).
Palittapongarnpim et al., Nucleic Acids Research 21(3) :761–762 (1993).
Feener et al., Am. J. of Human Genetics 48 :621–627 (1991).
Grist et al., Biotechniques 15(2) :304–309 (1993).
Litt et al., Am. J. of Human Genetics 44 : 397–401 (1989).
Brook et al., Cell 68 :799–808 (1992).
Gusella et al., Cell 72 :971–983 (1993).
Spada et al., Nature 352 :77–79 (1991).
Rosenthal et al., Nucleic Acids Research 18 (10) : 3095–3096 (1990).

*Primary Examiner*—W. Garn Jones
*Assistant Examiner*—Ethan Whisenant
*Attorney, Agent, or Firm*—Burns, Doane, Swecker & Mathis, L.L.P.

[57] ABSTRACT

The invention relates to a process for the selective amplification of restriction fragements comprising simple sequence repeats.

The process of the invention can be used in a range of fields including but not limited to plant and animal breeding, genetic identity testing in humans, plants and animals, disease identification and screening, forensic analysis and gene tagging and isolation.

15 Claims, 14 Drawing Sheets

FIG. 1   GENERAL METHOD FOR AMPLIFYING SIMPLE SEQUENCE REPEATS
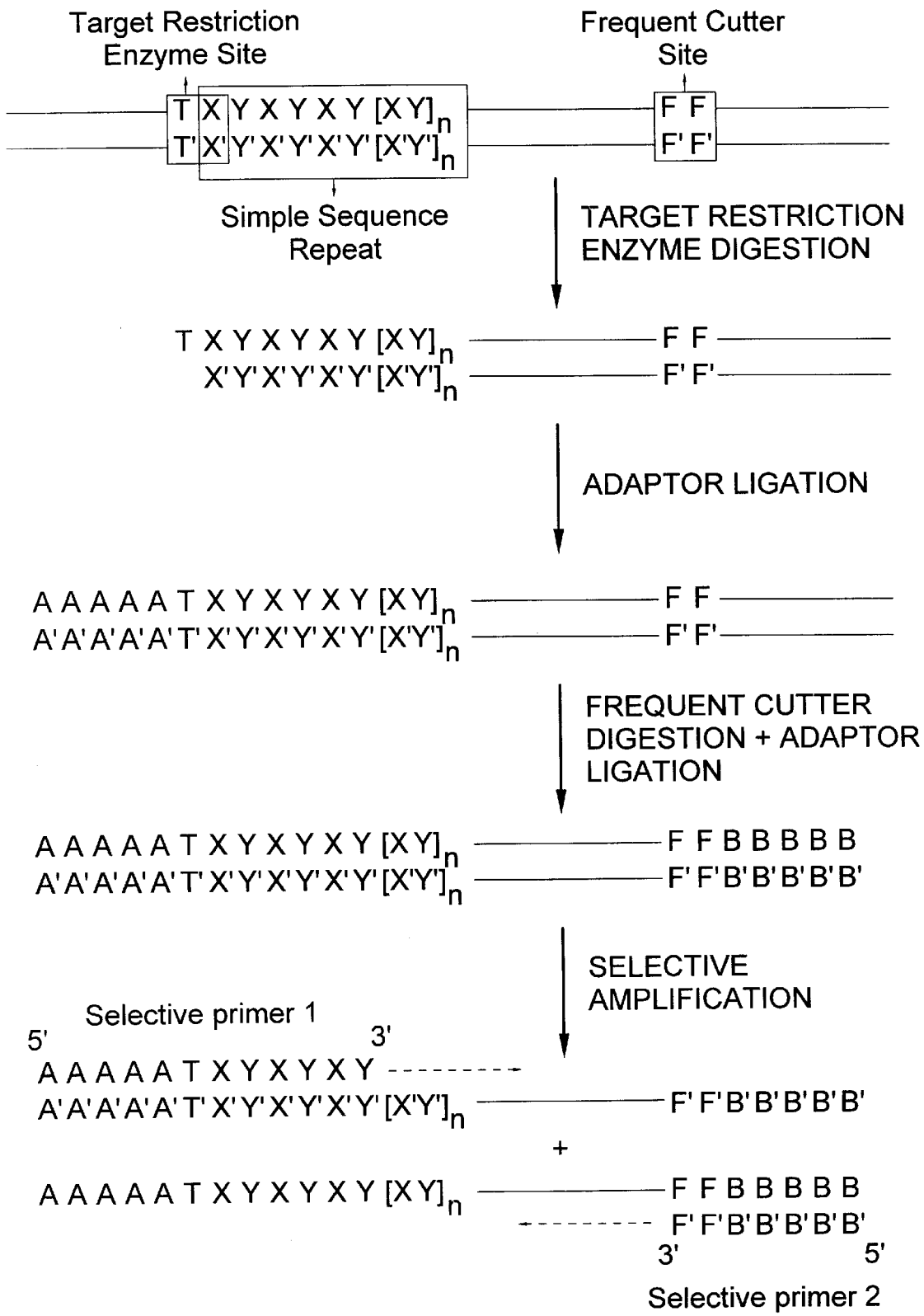

FIG. 2A  EXAMPLES OF PREFERRED RESTRICTION ENZYMES FOR TARGETING SIMPLE SEQUENCE REPEAT.

| REPEAT | RESTRICTION ENZYMES | SEQUENCE OVERLAP |
|---|---|---|
| $(A)_n$ | MseI | T$^\triangledown$TA$_\triangle$A , T$^\triangledown$TA$_\triangle$A |
| $(C)_n$ | AciI | C$^\triangledown$CG$_\triangle$C |
|  | MspI | C$^\triangledown$CG$_\triangle$G |
| $(AT)_n$ | MseI | T$^\triangledown$TA$_\triangle$AT |
|  | AseI | AT$^\triangledown$TA$_\triangle$AT |
| $(CA)_n$ | NlaIII | $_\triangle$CATG$^\triangledown$ |
|  | AflIII | A$^\triangledown$CGTG$_\triangle$T |
| $(GA)_n$ | AluI | AG$^\triangledown$$_\triangle$CT |
|  | BsmAI | GTCTCN$^\triangledown$ctct$_\triangle$ |
| $(GC)_n$ | AciI | C$^\triangledown$CG$_\triangle$C |
| $(AAT)_n$ | AseI | AT$^\triangledown$TA$_\triangle$AT |
|  | SspI | AAT$^\triangledown$$_\triangle$ATT |
| $(AAC)_n$ | MaeIII | $^\triangledown$GTAAC$_\triangle$ |
| $(AAG)_n$ | EarI | CTCTTCt$^\triangledown$tct$_\triangle$ |
| $(ATC)_n$ | BclI | T$^\triangledown$GATC$_\triangle$A |
|  | MboI | $^\triangledown$GATC$_\triangle$ |
|  | NlaIII | $_\triangle$CATG$^\triangledown$ |
| $(ACT)_n$ | MaeIII | $^\triangledown$GTTAC$_\triangle$ |
|  | BfaI | C$^\triangledown$TA$_\triangle$G |
| $(ACC)_n$ | Sau96I | G$^\triangledown$GAC$_\triangle$C |
|  | BanI | G$^\triangledown$GCAC$_\triangle$C |
|  | BstNI | CC$^\triangledown$T$_\triangle$GG |
|  | MaeIII | $^\triangledown$GTCAC$_\triangle$ |
| $(ACG)_n$ | TaqI | T$^\triangledown$CG$_\triangle$A |
|  | MaeII | A$^\triangledown$CG$_\triangle$T |
| $(AGC)_n$ | AlwNI CAG | $_\triangle$NNN$^\triangledown$CTG |
| $(AGG)_n$ | BstNI | CC$^\triangledown$A$_\triangle$GG |
|  | Sau96I | G$^\triangledown$GAC$_\triangle$C |

FIG. 2B

| Repeat | Enzyme | Recognition site |
|---|---|---|
| $(CGC)_n$ | BsiEI | C▽GG<u>CC</u>△G |
|  | EaeI | Py▽GG<u>CC</u>△G |
|  | BstUI | C<u>G</u>▽△<u>CG</u> |
|  | HaeIII | G<u>G</u>▽△<u>CC</u> |
| $(AAAT)_n$ | DraI | TT<u>T</u>▽△<u>AAA</u> |
|  | ApoI | A▽A<u>ATT</u>△T |
| $(AAAG)_n$ | DraI | TTT▽△<u>AAA</u>g |
|  | ApoI | gA▽<u>AATT</u>△T |
| $(AAAC)_n$ | DraI | TTT▽△<u>AAA</u>c |
|  | ApoI | cA▽<u>AATT</u>△T |
| $(AATG)_n$ | BspHI | T▽C<u>ATG</u>△A |
|  | NlaIII | △<u>CATG</u>▽ |
|  | EcoRI | <u>G</u>▽<u>AATT</u>△C |
|  | HinfI | <u>G</u>▽<u>AAT</u>△C |
| $(AATC)_n$ | BclI | T▽G<u>ATC</u>△A |
|  | HinfI | <u>G</u>▽<u>AAT</u>△C |
|  | MboI | ▽<u>GATC</u>△ |
|  | MunI | <u>C</u>▽<u>AATT</u>△G |
| $(AAGT)_n$ | DdeI | C▽<u>TAA</u>△G |
|  | AflII | C▽T<u>TAA</u>△G |
|  | MaeIII | ▽<u>GTTAC</u>△ |
| $(AAGC)_n$ | HindIII | <u>A</u>▽<u>AGCT</u>△T |
| $(AACT)_n$ | HpaI | GT<u>T</u>▽△<u>AAC</u> |
|  | MaeIII | ▽<u>GTAAC</u>△ |
|  | DdeI | C▽<u>TTA</u>△G |
|  | SpeI | A▽<u>CTAG</u>△T |
| $(AACG)_n$ | BstBI | TT▽<u>CG</u>△AA |
|  | MaeII | A▽<u>CG</u>△Tt |
| $(TATC)_n$ | BglII | A▽<u>GATC</u>△T |
|  | MboI | ▽<u>GATC</u>△ |
|  | SfcI | C▽<u>TATA</u>△G |
|  | XbaI | T▽<u>CTAG</u>△A |
| $(TAGG)_n$ | AvrII | C▽<u>CTAG</u>△G |

FIG. 2C

| | | |
|---|---|---|
| | SfcI | C▾TGTA▵G |
| | BamHI | G▾GATC▵C |
| | BstYI | G▾GATC▵C |
| (TAGC)ₙ | AciI | C▾CG▵C |
| (TACG)ₙ | | |
| (ATAC)ₙ | AccI | GT▾AT▵AC |
| | NdeI | CA▾TA▵TG |
| | NlaIII | ▵CATG▾ |
| (ATGG)ₙ | NcoI | C▾CATG▵G |
| | MboI | ▾GATC▵ |
| | NlaIII | ▵CATG▾ |
| (ATGC)ₙ | BsmI | GAATG▵Ca▾ |
| (ATCG)ₙ | TaqI | T▾CG▵At |
| | PvuI | CG▵AT▾CG |
| (AGAC)ₙ | BbsI | GAAGACag▾acag▵ |
| | SfcI | C▾TACA▵G |
| (AGTG)ₙ | DdeI | C▾TGA▵G |
| | HinfI | G▾ACT▵C |
| | MaeIII | ▾GTCAC▵ |
| (AGTC)ₙ | DdeI | C▾TCA▵G |
| | HinfI | G▾AGT▵C |
| | MaeIII | ▾GTGAC▵ |
| (AGGC)ₙ | BstNI | CC▾A▵GG |
| | PstI | C▵TGCA▾G |
| | ScrFI | CC▾A▵GG |
| (AGCG)ₙ | BstUI | CG▾▵CG |
| | AvaI | C▾PyCGA▵G |
| | TaqI | T▾CG▵Ac |
| | AciI | C▾CG▵Ct |
| | HgiAI | G▵WGCT▾C |
| (AGCC)ₙ | EaeI | Py▾GGCC▵A |
| | BstNI | CC▾T▵GG |
| | ScrFI | CC▾T▵GG |
| (ACGG)ₙ | BspEI | T▾CCGG▵A |

FIG. 2D

|  |  |  |
|---|---|---|
| | MaeII | A${}^{\triangledown}$CG${}_{A}$Tc |
| | AatII | G${}_{A}$ACGT${}^{\triangledown}$C |
| | AvaII | G${}^{\triangledown}$GTC${}_{A}$C |
| $(ACGC)_n$ | AciI | C${}^{\triangledown}$CG${}_{A}$Ca |
| | ApaLI | G${}^{\triangledown}$TGCA${}_{A}$C |
| | MaeII | A${}^{\triangledown}$CG${}_{A}$Tg |
| | AflIII | A${}^{\triangledown}$CGCG${}_{A}$T |
| | HgiAI | G${}_{A}$WGCA${}^{\triangledown}$C |
| $(ACCG)_n$ | AvaII | G${}^{\triangledown}$GAC${}_{A}$C |
| | TaqI | T${}^{\triangledown}$CG${}_{A}$Ac |
| | AgeI | A${}^{\triangledown}$CCGG${}_{A}$T |
| | Sau96I | G${}^{\triangledown}$GAC${}_{A}$C |
| $(ACCC)_n$ | BsrI | ACTG${}_{A}$Gg${}^{\triangledown}$ |
| | AciI | C${}^{\triangledown}$CG${}_{A}$C |
| $(AGGG)_n$ | Sau96I | G${}^{\triangledown}$GaC${}_{A}$C |
| $(GCCC)_n$ | ApaI | G${}_{A}$GGCC${}^{\triangledown}$C |
| | Sau96I | G${}^{\triangledown}$GCC${}_{A}$C |
| $(AATT)_n$ | SspI | AAT${}^{\triangledown}{}_{A}$ATT |
| | AseI | AT${}^{\triangledown}$TA${}_{A}$AT |
| $(AAGG)_n$ | BsaJI | C${}^{\triangledown}$CAAG${}_{A}$G |
| | EarI | CTCTTCc${}^{\triangledown}$ttc${}_{A}$ |
| | StyI | C${}^{\triangledown}$CAAG${}_{A}$G |
| $(AACC)_n$ | BsaJI | C${}^{\triangledown}$CAAG${}_{A}$G |
| | BsrI | ACTG${}_{A}$Gt${}^{\triangledown}$ |
| | StyI | C${}^{\triangledown}$CAAG${}_{A}$G |
| $(GGCC)_n$ | BsaJI | C${}^{\triangledown}$CCCG${}_{A}$G |

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTCTCNNNNN                                                                                              10

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTCTCTCTCT                                                                                              10

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GACGATGAGT CCTGAG                                                                  16

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TACTCAGGAC TCAT                                                                           14

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTCGTAGACT GCGTACC                                                                                  17

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCTGACGCAT GGGAGA                                                                                   16

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GACTGCGTAC CCTCTCTC                                                                                 18

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GATGAGTCCT GAGTAAT                                                                                  17

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GACTGCGTAC CCTCTCTCTC T                                                                             21

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATGAGTCCT GAGTAATCT                                                                                19

( 2 ) INFORMATION FOR SEQ ID NO:11:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

GATGAGTCCT GAGTAATCA    19

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTCTTCNNNN    10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CTCTTCTTCT    10

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TCTGACGCAT GGAGA    15

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GACTGCGTAC CTCTTC    16

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:16:

GATGAGTCCT GAGTAAA 17

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

GACTGCGTAC CTCTTCTTC 19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

GATGAGTCCT GAGTAAATT 19

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

CTCTTCCTTC 10

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

TCTGACGCAT GGAAG 15

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:21:

```
GACTGCGTAC CTTCCT                                                                                 16
```

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GACTGCGTAC CTTCCTTCC                                                                              19
```

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
CTCGTAGACT GCGTACA                                                                                17
```

(2) INFORMATION FOR SEQ ID NO:24:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
CATCTGACGC ATGT                                                                                   14
```

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
GTAGACTGCG TACAAAATAA                                                                             20
```

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
GATGAGTCCT GAGTAATA                                                                               18
```

(2) INFORMATION FOR SEQ ID NO:27:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

GTAGACTGCG TACAAAATAA ATA 23

( 2 ) INFORMATION FOR SEQ ID NO:28:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

GATGAGTCCT GAGTAATATC 20

( 2 ) INFORMATION FOR SEQ ID NO:29:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:29:

CTCGTAGACT GCGTACCCAT G 21

( 2 ) INFORMATION FOR SEQ ID NO:30:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:30:

TCTGACGCAT GG 12

( 2 ) INFORMATION FOR SEQ ID NO:31:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:31:

CTGCGTACCC ATGTGT 16

( 2 ) INFORMATION FOR SEQ ID NO:32:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:32:

GATGAGTCCT GAGTAAA 17

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GCGTACCCAT GTGTGTG 17

( 2 ) INFORMATION FOR SEQ ID NO:34:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TCTGACGCAT GTGATC 16

( 2 ) INFORMATION FOR SEQ ID NO:35:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CTGCGTACAC TAGATA 16

( 2 ) INFORMATION FOR SEQ ID NO:36:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

GATGAGTCCT GAGTAA 16

( 2 ) INFORMATION FOR SEQ ID NO:37:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GCGTACACTA GATAGAT    17

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GATGAGTCCT GAGTAACT    18

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

TCTAGATAGA TAGATANNNT TAA    23

( 2 ) INFORMATION FOR SEQ ID NO:40:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

AGATCTATCT ATCTATNNNA ATT    23

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

CTAGATAGAT AGATANNNTT A    21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

GATCTATCTA TCTATNNNAA T    21

( 2 ) INFORMATION FOR SEQ ID NO:43:

( i ) SEQUENCE CHARACTERISTICS:
　　( A ) LENGTH: 23 base pairs
　　( B ) TYPE: nucleic acid
　　( C ) STRANDEDNESS: single
　　( D ) TOPOLOGY: linear ( i i ) MOLECULE TYPE: DNA (genomic)

( x i ) SEQUENCE DESCRIPTION: SEQ ID NO:43:

GTCTCTCTCT CTCTCTNNNT TAA　　　　　　　　　　　　　　　　　　23

( 2 ) INFORMATION FOR SEQ ID NO:44:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:44:

CAGAGAGAGA GAGAGANNNA ATT　　　　　　　　　　　　　　　　　　23

( 2 ) INFORMATION FOR SEQ ID NO:45:

( i ) SEQUENCE CHARACTERISTICS:
　　　　( A ) LENGTH: 16 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:45:

CTCTCTCTCT NNNTTA　　　　　　　　　　　　　　　　　　　　　　　16

( 2 ) INFORMATION FOR SEQ ID NO:46:

( i ) SEQUENCE CHARACTERISTICS:
　　　　( A ) LENGTH: 16 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:46:

GAGAGAGAGA NNNAAT　　　　　　　　　　　　　　　　　　　　　　　16

( 2 ) INFORMATION FOR SEQ ID NO:47:

( i ) SEQUENCE CHARACTERISTICS:
　　　　( A ) LENGTH: 16 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:47:

GAGAGAGAGA NNNAAT　　　　　　　　　　　　　　　　　　　　　　　16

AMPLIFICATION OF SIMPLE SEQUENCE REPEATS

TECHNICAL FIELD/FIELD OF THE INVENTION

This invention relates to applications of DNA fingerprinting and the use of DNA markers in a range of fields including but not limited to plant and animal breeding, genetic identity testing in humans, plants and animals, disease identification and screening, forensic analysis and gene tagging and isolation. More specifically, this invention relates to general methods for DNA fingerprinting based on the selective amplification of restriction fragments comprising simple sequence repeats. The invention relates also to synthetic DNA molecules and products based thereon which are used in the methods of the invention in the different fields of application.

BACKGROUND OF THE INVENTION

The use of PCR based methods in DNA fingerprinting has rapidly expanded the range of applications of DNA typing and genetic analysis in as widely diverse fields as microbial typing, plant and animal breeding and human genetic testing. These methods detect minor variations in the genetic material, termed DNA polymorphisms. The major limitation of current DNA typing technologies stems from the lack of DNA polymorphism in the genetic material under study. In general, DNA polymorphism results from random mutations, nucleotide changes or insertions and deletions, which have accumulated in the genetic material of each biological species. In certain species the frequency of random mutations appear to be high, while in other species such mutations occur rarely. As a consequence, DNA fingerprinting methods detecting random mutations will be highly informative in the former but not in the latter, thus severely limiting the use of DNA typing in the latter class of biological species. To overcome this limitation, DNA typing methods have been developed which target DNA segments or DNA sequences which exhibit a much higher degree of variability. One such type of hypervariable DNA sequences are the so called simple sequence repeats. These are DNA sequences composed of tandemly repeated sequences of one, two, three or four nucleotides. Occasionally repeat units of more than four nucleotides are observed. Such sequences generally exhibit a variation in the number of tandemly repeated units in genetic material and it is generally believed that this variation in repeat number arises from a high error rate during DNA replication. Since each repeat number of a simple sequence repeat constitutes a different allelic form, DNA markers based on simple sequence repeats are the most informative marker type currently available. The limitations of using simple sequence repeat DNA markers are twofold: (a) the development of these markers is extremely laborious and time consuming and needs to be repeated for each biological species and (b) the detection of these markers is limited to single locus assay systems in which the DNA markers are individually identified in separate PCR reactions.

In view of these limitations there is a strong need for DNA typing methods which would allow simple sequence repeat markers to be detected and isolated more efficiently, so as to broaden the range of applications of simple sequence repeat based marker systems.

It is the objective of the present invention to provide an efficient and generally applicable DNA fingerprinting method which obviates the heed for the laborious step in simple sequence repeat marker isolation and which provides a simple method for detecting a large number of simple sequence repeat markers in single multilocus assays.

The main problem in identifying simple sequence repeats in the genomes of biological species is that such sequences in general occur very infrequently, and hence very rarely appear in random DNA fingerprints. In the present invention we have devised a method for selectively amplifying simple sequence repeats in DNA and which can be displayed in DNA fingerprints. This method is based on an earlier invention in which a DNA fingerprinting method was developed to selectively amplify restriction fragments (EP0534858). In essence, the method for selective restriction fragment amplification as described in European Patent Application EP0534858 consists of digesting genomic DNA with restriction enzymes, ligating synthetic oligonucleotide adaptors to the ends, using "selective PCR primers" to amplify a subset of the restriction fragments, and fractionating the amplified fragments on an appropriate gel system. The selective principle resides in the design of the selective PCR primers. In general, these primers are composed of a sequence which matches the common sequences at the ends of the restriction fragments and a variable number of random nucleotides referred to as selective nucleotides, added to the 3'end of the common sequence. These selective nucleotides will ensure that only those restriction fragments exhibiting a matching sequence will be amplified. Since the 3'nucleotides must match perfectly in order for the PCR primers to efficiently amplify their target DNA fragment, this selective principle exhibits a very high degree of fidelity. This ensures that only those fragments having a perfect match to the selective nucleotides used will be amplified. Furthermore it has to be realized that the selection is applied at both ends simultaneously since both DNA strands need to be copied in order to achieve an exponential amplification in the PCR reaction. Extensive research has shown that the selective restriction fragment amplification method can be used effectively on DNA from any biological species to yield highly reproducible and detailed DNA fingerprints.

The preferred procedure for the selective restriction fragment amplification uses a combination of two different restriction enzymes: one enzyme which serves the purpose of targeting rare sequences (a rare cutter restriction enzyme) and a second enzyme (a frequent cutter enzyme) which serves the purpose of reducing the size of the restriction fragments to a range of sizes which are amplified efficiently. By targeting rare sequences one basically reduces the complexity of the starting mixture of DNA fragments, and hence one is able to achieve a more reliable and accurate amplification.

The DNA fingerprinting method for selective restriction fragment amplification detects two types of DNA markers: (a) dominant markers based on point mutations and (b) codominant markers based on insertions or deletions. In different DNAs with a high percentage of sequence polymorphism the method for selective restriction fragment amplification will generate lots of dominant markers. These dominant markers are mono-allelic. In more closely related DNAS, marker bands will be much less frequent, and consequently more fingerprints will have to be run in order to obtain enough markers. Moreover, the frequency in which codominant markers are detected is much lower than dominant markers. The simple sequence repeats constitute a special type of codominant marker. These repetitive elements usually display a high degree of length polymorphism. Moreover, there are often multiple alleles of these markers, giving these a high Polymorphism Information Content (PIC).

The method of the present invention provides an efficient and generally applicable DNA fingerprinting method in which preferably codominant markers are generated.

DISCLOSURE OF THE INVENTION

In the present invention we have developed a novel targeting principle in which we use a combination of a targeting restriction enzyme and a targeting selective PCR primer such that the selectively amplified restriction fragments are enriched for simple sequence repeats. A simple sequence repeat refers to a DNA sequence composed of at least two tandemly repeated simple sequence repeat units of one, two, three, four or more nucleotides. The principle of the invention, illustrated in FIG. 1 and schematically represented in FIG. 9, is to use a targeting restriction enzyme which is chosen in such a way that its recognition sequence overlaps with or precisely flanks a chosen simple sequence repeat. In this way one obtains a mixture of restriction fragments comprising restriction fragments which carry the targeted simple sequence repeat precisely at one end of the restriction fragment. After ligating an appropriate double stranded synthetic oligonucleotide (referred to as "adaptor") to the ends generated by the targeting restriction enzyme one obtains restriction fragments having a common sequence at their ends, comprising a set of restriction fragments in which the targeted simple sequence repeat is flanked by a common sequence. In essence this process replaces one of the two variable sequences flanking the simple sequence repeats by a common sequence. This then allows the design of generic PCR primers comprising the common sequence and part of the repeated sequence to selectively amplify the restriction fragments carrying the targeted simple sequence repeat. The common sequence comprises the adaptor sequence and optionally, depending on the restriction enzyme used, further comprises the recognition sequence or part thereof and/or the cleavage site or part thereof. The next step in the process is to cleave the DNA with a frequent cutter restriction enzyme which serves the general purpose of reducing the size of the restriction fragments generated by the targeting enzyme to a size range compatible with efficient PCR amplification and to ligate an appropriate adaptor to the ends generated by the frequent cutter restriction enzyme. It should be understood by the person skilled in the art that this step can be carried out simultaneously with the cleavage and ligation step involving the targeting restriction enzyme. The choice of the targeting restriction enzyme is based on the type of simple sequence repeat to be targeted. The choice of the second enzyme depends on the type of target DNA under study, the estimated frequency of recognition sites for the second enzyme present in the target DNA and the estimated sizes of the restriction fragments that will be obtained in combination with the targeting enzyme. In the following steps the restriction fragments carrying the targeted simple sequence repeat are amplified using two different PCR primers with the following general design: primer one having a sequence at the 5'end matching the common sequence at the end of the restriction fragment produced by the first restriction enzyme and appropriate adaptor ligation and at the 3'end at least 5 nucleotides matching the sequence of the simple sequence repeat; primer two having a sequence at the 5'end matching the common sequence at the end of the restriction fragment produced by the second restriction enzyme and appropriate adaptor ligation and at its 3'end ranging from 0, 1, 2, 3, 4 or more randomly chosen selective nucleotides. A sequence matching a defined sequence refers to a sequence that has the same nucleotide sequence as the corresponding strand, or a complementary sequence to the opposite strand, of the defined sequence or part thereof. The PCR products obtained in accordance with the invention can be identified using standard fractionation methods, such as gel electrophoresis using standard gel matrices. If a given target enzyme would generate more restriction fragments containing the targeted repeats than can be displayed on a single gel one can use an appropriate number of selective nucleotides in the selective primer for the frequent cutter end to obtain a discrete number of amplified fragments.

The method according to the present inventions is not restricted to the use of two different restriction enzymes: one can also use one or more targeting restriction enzymes in combination with one or more frequent cutting restriction enzymes.

The present invention relates to a general method for DNA fingerprinting based on the selective amplification of restriction fragments comprising simple sequence repeats obtained for example by digesting genomic DNA from animals, plants or humans with restriction enzymes and comprising the following steps: (a) digesting the starting DNA with two or more different restriction enzymes, at least one enzyme cleaving at or near its recognition sequence which overlaps or flanks the simple sequence repeat (referred to as first restriction enzyme) and at least one enzyme preferably cleaving in a four-base sequence (referred to as second restriction enzyme), (b) ligating a different double stranded oligonucleotide adaptor to each of the ends of the fragments produced by said restriction enzymes, the adaptors being designed in such a way that they have one end matching the 5'end produced by the corresponding restriction enzyme, (c) selectively amplifying the restriction fragments using two or more different PCR primers with the following general design: one primer having a sequence at the 5'end matching the sequence of the adaptor of the first restriction enzyme and its recognition site, or part thereof, and at the 3'end at least 5 nucleotides matching the sequence of the simple sequence repeat (referred to as primer one); one primer having a sequence at the 5'end matching the sequence of the adaptor of the second restriction enzyme and its recognition sequence, or part thereof, and at its 3'end ranging from 0, 1, 2, 3, 4 or more randomly chosen nucleotides (referred to as primer two).

Preferably the recognition sequence of the targeting restriction enzyme is located immediately adjacent to the simple sequence repeat.

In a preferred embodiment of the present invention, the selective amplification of the restriction fragments comprising the simple sequence repeats is carried out in a cascade of consecutive steps of selective amplification reactions using selective primers with increasing selectivity, i.e. with increasing number of selective nucleotides at the 3'end of the primer. Each step forms an enrichment step for restriction fragments comprising simple sequence repeats.

In a preferred embodiment of the invention, the preferred choice of the restriction enzyme used to target a particular simple sequence repeat is such that its recognition sequence overlaps maximally with the repeated sequences. The recognition sequence comprises perferably at least one simple sequence repeat unit or part thereof and at least one non overlapping nucleotide with the simple sequence repeat unit. The rationale for maximal overlap is that one can amplify in this way the largest possible number of repeated sequences present in the genome under study. For example, the restriction enzyme HinfI can be used to target the following four-base repeats: $(ATTC)_n$, $(AATC)_n$, $(ACTC)_n$ and (AGTC)$_n$. In each case, 4 of the 5 nucleotides of the HinfI recognition sequence GANTC overlap with the repeat, leaving only one non overlapping nucleotide. With this targeting enzyme one will be able to amplify 25% (one in four) of all occurring repeats. Another example comprises the restriction enzyme MaeIII which targets the three-base repeat (AAC)$_n$. In this case only three of the five nucleotides of the MaeIII recognition site GTNAC overlap with the repeat leaving two flanking non overlapping nucleotides. This enzyme will thus only target one of sixteen occurring (AAC)$_n$ repeats, namely those flanked by the dinucleotide GT. In the case of three non overlapping nucleotides, the number of targeted repeats is only one out of sixty four. FIG. 2 lists the preferred restriction enzymes that can be used to target different two-, three- and four-base repeats.

The targeting restriction enzymes can be chosen from the group of Type 1 or Type 2 restriction enzymes. Type 1 restriction enzymes are palindromic restriction enzymes that cleave the strands of the nucleic acid within the recognition sequence. A schematic representation is provided in FIG. 10 wherein XbaI is an example of a Type 1 restriction enzyme.

In a more preferred embodiment of the invention, the targeting restriction enzyme belongs to the group of Type 2 restriction enzymes. Type 2 restriction enzymes are non-palindromic restriction enzymes that cleave the strands of the nucleic acid outside the recognition sequence. The use of Type 2 restriction enzymes allows an additional selection for simple sequence repeats. The additional selection is obtained by the use of oligonucleotide adapters which have at one end a single stranded extension having a sequence that match the sequence of one or more simple sequence repeat units or part thereof. Only those restriction fragments having a complementary single stranded extension to the single stranded extension of the oligonucleotide adaptor will be ligated to the adaptor. A schematic representation is provided in FIG. 11 wherein BsmAI is an example of a Type 2 restriction enzyme. In the following step these restriction fragments are selectively amplified using two different PCR primers with the following general design: primer one having a sequence at the 5'end matching the sequence of the adaptor of the first restriction enzyme followed by a sequence matching the sequence of the recognition site of the first restriction enzyme, or part thereof, and a sequence matching the extension and at the 3'end at least 5 nucleotides matching the sequence of the simple sequence repeat; primer two having a sequence at the 5'end matching the sequence of the adaptor of the second restriction enzyme and its recognition sequence and at its 3'end ranging from 0, 1, 2, 3, 4 or more randomly chosen nucleotides.

The sequence of the selective nucleotides at the 55 end of primer one comprises at least one simple sequence repeat unit, or part thereof, having a sequence which is in phase with the sequence of the simple sequence repeat, or part thereof, which is present in the recognition site of the first restriction enzyme.

Fingerprints of sets of simple sequence repeats can be obtained according to the method of the invention using a panel of frequent-cutter primers (primer two), combined with a fixed targeting primer (primer one).

In a preferred embodiment of the invention the digestion and ligation step is carried out in one step. In order to obtain restriction fragments with ligated adaptors to both ends of the fragment, the adaptors are designed such that one end is compatible to be ligated to the ends of the restriction fragment and that, after ligation, the recognition sites of the restriction enzymes are not restored.

The starting DNA can be genomic DNA from eukaryotes such as plants, animals or human beings or fragments thereof.

The method of the present inventions allows the detection of multiple alleles of one locus. Moreover, the method of the present inventions allows the detection of multiple loci within one assay.

The present invention relates furthermore to a kit for the application of the method according to the invention comprising the restriction enzymes as described above, double stranded synthetic oligonucleotide sequences, and the selective primers according to the invention.

The amplified fragments obtained by the process of the invention can be fractionated on a gel to obtain DNA fingerprinting.

The following examples and figures provide an illustration of the invention which is nevertheless not limited to these examples.

BRIEF DESCRIPTION OF THE FIGURES

FIG. 1 provides a graphic outline for the general concept of selective amplification of restriction fragments containing simple sequence repeats. The letters denote the following:
X: any sequence of 0, 1, 2, or 3 nucleotides
Y: any nucleotide
XY: simple sequence repeat unit of 1, 2, 3, or 4 nucleotides
[XY]$_n$: simple sequence repeat comprising n repeat units
X'Y': sequence complementary to XY
T: non overlapping nucleotides
TX: target restriction site sequence
T'X': complementary sequence of TX
FF: frequent cutter restriction site sequence
F'F': sequence complementary to FF
AAAAA: sequence of the synthetic adaptor ligated to the cleaved TX site
BBBBB: sequence of the synthetic adaptor ligated to the cleaved FF site
AAAAAT[XY]$_n$: general design of the specific PCR primer used to selectively amplify restriction fragments FIG. 2 depicts examples of preferred restriction enzymes for targeting simple sequence repeats. The simple sequence repeat or parts of the repeat or its complementary sequence has been underlined in the recognition site. The restriction enzyme cleavage site has been indicated by arrow heads.

EXAMPLES

Example 1

Figure 3:
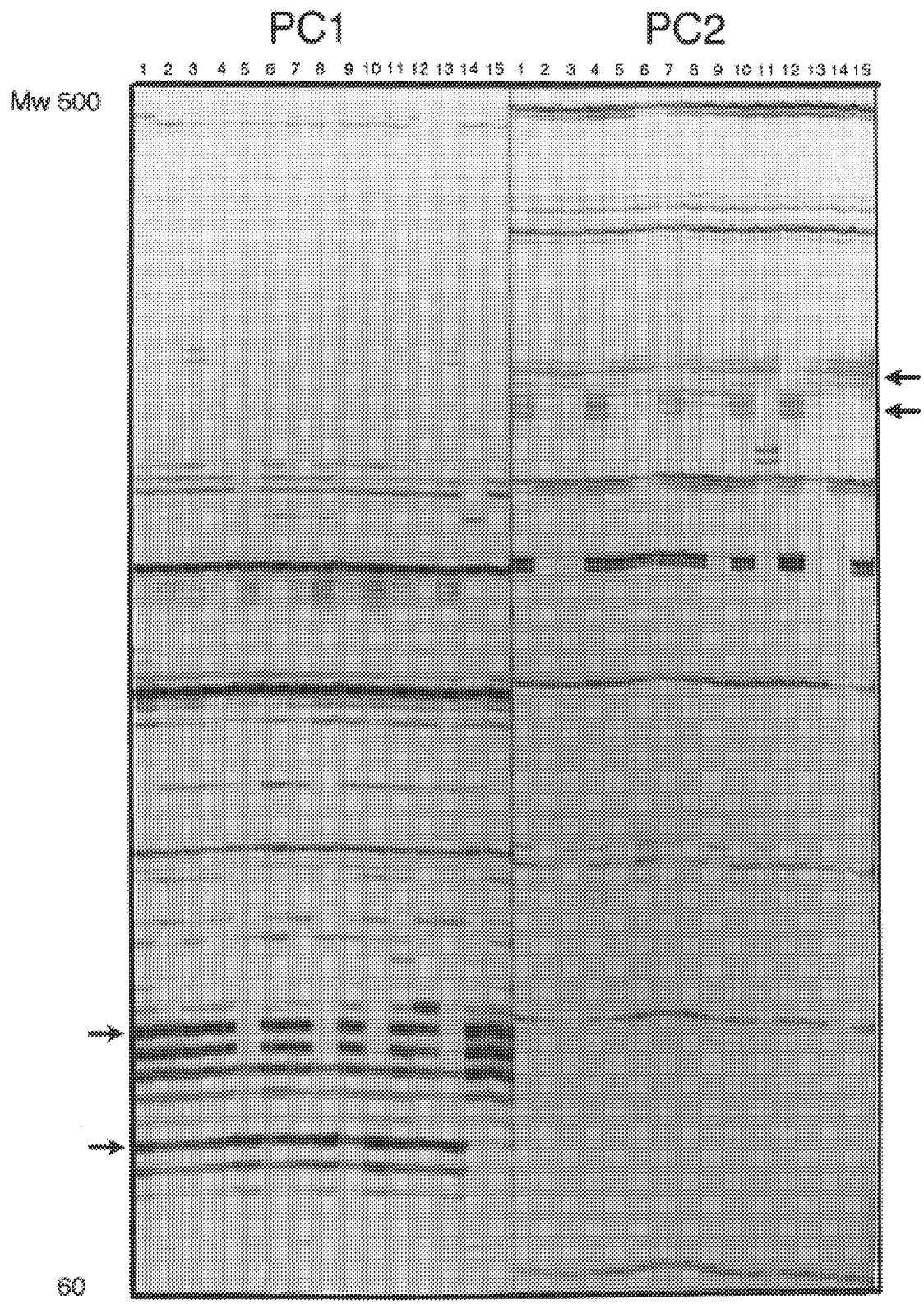
FIG. 3 illustrates the targeting of the (TC)$_n$ repeat with the restriction enzyme BsmAI. The figure displays the electropherogram analyzed on a standard 4.5% polyacrylamide gel. The figure contains two panels (PC1 and PC2), containing products amplified with the BsmAI +6 primer in combination with an MseI primer +3 containing the 3' extension -TCT (panel I) or the 3' extension -TCA (panel II). DNAs analyzed in these panels were from CEPH family 1423, members 1 through 15. Products range in size from 60 nucleotides to 500 nucleotides, as indicated in the left margin of the figure. Arrows point to clear examples of codominant simple sequence repeat containing markers.

Targeting of the $(TC)_n$ Motif with the Restriction Enzyme BSMAI.

Introduction

BamAI recognizes the sequence [SEQ ID NO.: 1] G TCTCn$^v$nnnn·. For targeting $(TC)_n$ repeats (also referred to as motifs or repeat motifs) a specific form of this recognition sequence [SEQ ID NO.: 2], GTCTCt$^v$ctct· is targeted. In this example, as in examples 2 and 3, a restriction enzyme is used that cuts outside its recognition sequence. This produces an overhang that allows selection in the ligation by using a specific adapter sequence. Here, an adapter is used to allow selection for a $(TC)_n$ motif in the ligation reaction. The strategy is further illustrated in FIG. 11.

A) Isolation and modification of the DNA

The first step of the template preparation is restriction of the DNA with the rare-cut restriction enzyme and MseI (T/TAA) as frequent-cutter. Generally for targeting repeat motifs, a buffer is used in which both enzymes work well, and that is also suitable for the subsequent ligation reaction. The DNA is restricted for a minimum of 1 hour at 37° C. The majority of DNA fragments should be <500 bp for high quality AFLP fingerprints. MseI (TTAA) gives small DNA fragments in most plant- and animal species. Thus, the DNA is trimmed down to a size that is amplified well in the subsequent polymerase chain reaction (PCR).

In example 1, the strategy was tested on DNA from the human family 1423 made available by CEPH (Centre d'Etude du Polymorphisme Humain, Paris, France). First, the human DNA was cut with a combination of two enzymes: BsmAI, targeting the boundary of a simple sequence repeat motif, and MseI. The reaction conditions for restricting the DNA were:

0.5 micro gram DNA
5 units BsmAI (the rare-cutter, New England Biolabs)
10 mM Tris.HAc pH 7.5
10 mM MgAc
50 mM KAc
5 mM DTT
50 ng/micro liter BSA.

In a total volume of 40 micro liters.

The restriction reaction was started at a temperature of 55° C., a temperature optimal for BsmAI. After 1 hour, 5 units MaeI (N. E. Biolabs) was added and the incubation was continued for another hour, at 37° C.

Following the restriction of the DNA, two adapters are ligated to the restriction fragments. The MseI adapter has the following structure [SEQ ID NOS.: 3–4]:

| | | |
|---|---|---|
| 5- | GACGATGAGTCCTGAG | -3 |
| 3- | TACTCAGGACTCAT | -5 |

The design [SEQ ID NOS.: 5–6] and use of the MseI adapter has already been described in European Patent Application EP0534858. All rare-cut adapters used in this and the next series of examples are prepared using the same molarity of oligo-nucleotides as described in EP0534858.

The BsmAI adapter has the following design:

| | | |
|---|---|---|
| 5-biotin-CTCGTAGACTGCGTACC | | -3 |
| 3- | TCTGACGCATGGGAGA | -5 |

This BsmAI adapter contains a bottom strand starting with the sequence 5-AGAG. With this design, the adapter can only be ligated to 1 out of 256 possible permutations of a sequence of 4 nucleotides (NNNN) present as 5'-overhang on BsmAI fragments: 5-CTCT. This sequence contains two repeat motifs of the type (CT).

The adapters are designed in such a way that the restriction sites are not restored after ligation. During the ligation reaction the restriction enzymes are still active. In this way fragment-to-fragment ligation is suppressed, since fragment concatamers are restricted. Adapter-to-adapter ligation is not possible because the adapters are not phosphorylated.

The ligation of adapters was done as described in European Patent Application EP0534858. Next, template molecules were purified by separating the biotinylated fragments from the non-biotinylated fragments as described (European Patent Application EP0534858).

B) Amplification of template molecules containing a repeat-motif boundary.

Following modification of the DNA, and preparation of template DNA, two amplification steps were performed, to target simple sequence repeat motifs. In a selective restriction fragment amplification reaction, also referred to as AFLP reaction, the selectivity of the AFLP-primers is generally good with 3' extensions up to 3 selective nucleotides long. When longer extensions are used, the selective amplification is preferably done in consecutive steps. In each step no more than 3 nucleotides in the extension must be selective for a subset from a template DNA mixture. Thus, in each step good selectivity is guaranteed. The targeting of simple sequence repeat motifs requires the use of extensions with at least 5 selective nucleotides. In step 1 the maximum number of 3 selective nucleotides may be used (preamplification), in the final amplification the extension contains the full 5 or more selective nucleotides that are necessary to target the repeat-motif. Modifications of this procedure may use fewer selective nucleotides in extensions at any given step, depending on the total number of extension nucleotides necessary to obtain fingerprints with fragment numbers that can be resolved well on sequencing gels.

Following the preamplification step, the preamplified template mixture was used as template in an AFLP reaction, using in one of the AFLP primers a specific extension with 6 nucleotides specifying the simple sequence repeat motif. The other AFLP primer in these examples is a standard MseI primer. In this example, the procedure is described for targeting of $(CT)_n$ motifs, with BsmAI as the rare-cut enzyme. Other sequence motifs are targeted each with their own combination of restriction enzyme, adapter sequence and primers.

The two consecutive PCR reactions were performed as follows:

A 50 micro liter reaction mixture was assembled containing the following components:
5 micro liters resuspended biotinylated template
30 ng unlabelled BsmAI primer 1a
30 ng unlabelled MseI primer 2a
0.8 mM dNTPs
1.5 mM MgCl2
50 mM KCl
10 mM Tris-Cl pH=8.3
0.4U Taq-polymerase (Perkin Elmer)
PCR conditions were:
Cycle-profile for a Perkin Elmer 9600 thermo cycler:

| | |
|---|---|
| 30 sec 94° C. denaturation | |
| 30 sec 65° C. annealing | cycle 1 |
| 60 sec 72° C. extension | |

| | |
|---|---|
| Lower annealing temperature each cycle 0.7° C. during 12 cycles | cycle 2–13 |
| 30 sec 94° C. denaturation | |
| 30 sec 56° C. annealing | cycle 14–36 |
| 60 sec 72° C. extension | |

The second step in the two-step AFLP reaction has the sane cycle profile as the first step. A small portion from the reaction mixture of the first amplification step is used as starting material for the second amplification step. For this purpose the first step amplification products are diluted 20-fold in T0.1E, and 5 micro liter is taken for each AFLP reaction. The reaction mixture for the second step amplification contains the following components:
5 micro liters 20-fold diluted preamplification mixture
5 ng $^{33}$P-radiolabelled BsmAI primer 1b
30 ng unlabelled MseI primer 2b
0.8 mM dNTPs
1.5 mM MgCl2
50 mM KCl
10 mM Tris-Cl pH=8.3
0.4U Taq-polymerase (Perkin Elmer)

Labelling of primers was carried out as described (European Patent Application EP0534858)

The primers [SEQ ID NO.: 7] that are used in this example are:

Step 1

| |
|---|
| BsmAI primer [SEQ ID NO.:8] 1a: 5-GACTGCGTACCCTCTCTC |

This primer contains a total of 3 selective nucelotides, also indicated as +3. In the following primers this short notation of the length of the extension is used.

| | |
|---|---|
| MseI primer 2a: | 5-GATGAGTCCTGAGTAAT (+1) |

Step 2
Primer combination 1 (PC1) [SEQ ID NOS.: 9–10]

| | | |
|---|---|---|
| BsmAI primer 1b: | 5-$^{33}$P-GACTGCGTACCCTCTCTCTCT | (+6) |
| MseI primer 2b: | 5-GATGAGTCCTGAGTAATCT | (+3) |

Primer combination 2 (PC2) [SEQ ID NOS.: 9 and 11]

| | | |
|---|---|---|
| BsmAI primer 1b: | 5-$^{33}$P-GACTGCGTACCCTCTCTCTCT | (+6) |
| MseI prixner 2b: | 5-GATGAGTCCTGAGTAATCA | (+3) |

C) Analysis of amplified products

Radiolabelled products from the second amplification reaction were analyzed as described in European Patent Application EP0534858. The products of the reaction are displayed in FIG. 3.

Example 2

Targeting of the $(CTT)_n$ Motif with the Restriction Enzyme EARI

The restriction enzyme EarI recognizes the sequence [SEQ ID NO.: 12] CTCTTCn$^v$nnn.. For targeting $(CTT)_n$ motifs a specific form of this recognition sequence [SEQ ID NO.: 13], CTCTTCt$^v$tct, is targeted. In this example, as in example 1, a restriction enzyme is used that cuts outside its recognition sequence. This produces an overhang that allows selection in the ligation by using a specific adapter sequence. The strategy is further illustrated in FIG. 11. In case of targeting $(CTT)_n$ motifs, the elements of the figure corresponding to the rare-cutter, and the adapter- and primer sequences have to be substituted by sequences described here, for example 2.

A) Isolation and modification of the DNA

For this example we isolated DNA from 4 anonymous breeding lines of pepper. DNA was isolated using a CTAB procedure described by Stewart and Via (1993) Biotechniques 14, 748–750. DNAs were restricted and modified as described in example 1, with the exception that the enzyme EarI cuts at 37° C., allowing the co-digestion of DNA with EarI and MseI. Templates were prepared and amplified as described in example 1. This required a specific adapter for the 3'-AGA overhang produced by the EarI restriction enzyme:

The EarI adapter for targeting $(TTC)_n$ motifs has the following design [SEQ ID NOS.: 5 AND 14]:

5-biotin-CTCGTAGACTGCGTACC
TCTGACGCATGGAGA-5

Note, that this EarI adapter contains a bottom strand specifically targeted to the sequence 5'-TCT.

B) Amplification of template DNA

In the subsequent amplification reactions the following primers [SEQ ID NOS.: 15–18] are used:

Step 1

| EarI primer 1a: | 5-GACTGCGTACCTCTTC | (+2) |
| MseI primer 2a: | 5-GATGAGTCCTGAGTAAA | (+1) |

Step 2

| EarI primer 1b: | 5-³³P-GACTGCGTACCTCTTCTTC | (+5) |
| MseI primer 2b: | 5-GATGAGTCCTGAGTAAATT | (+3) |

Amplification of products was performed as described in example 1.

C) Analysis of amplified products

Figure 4:
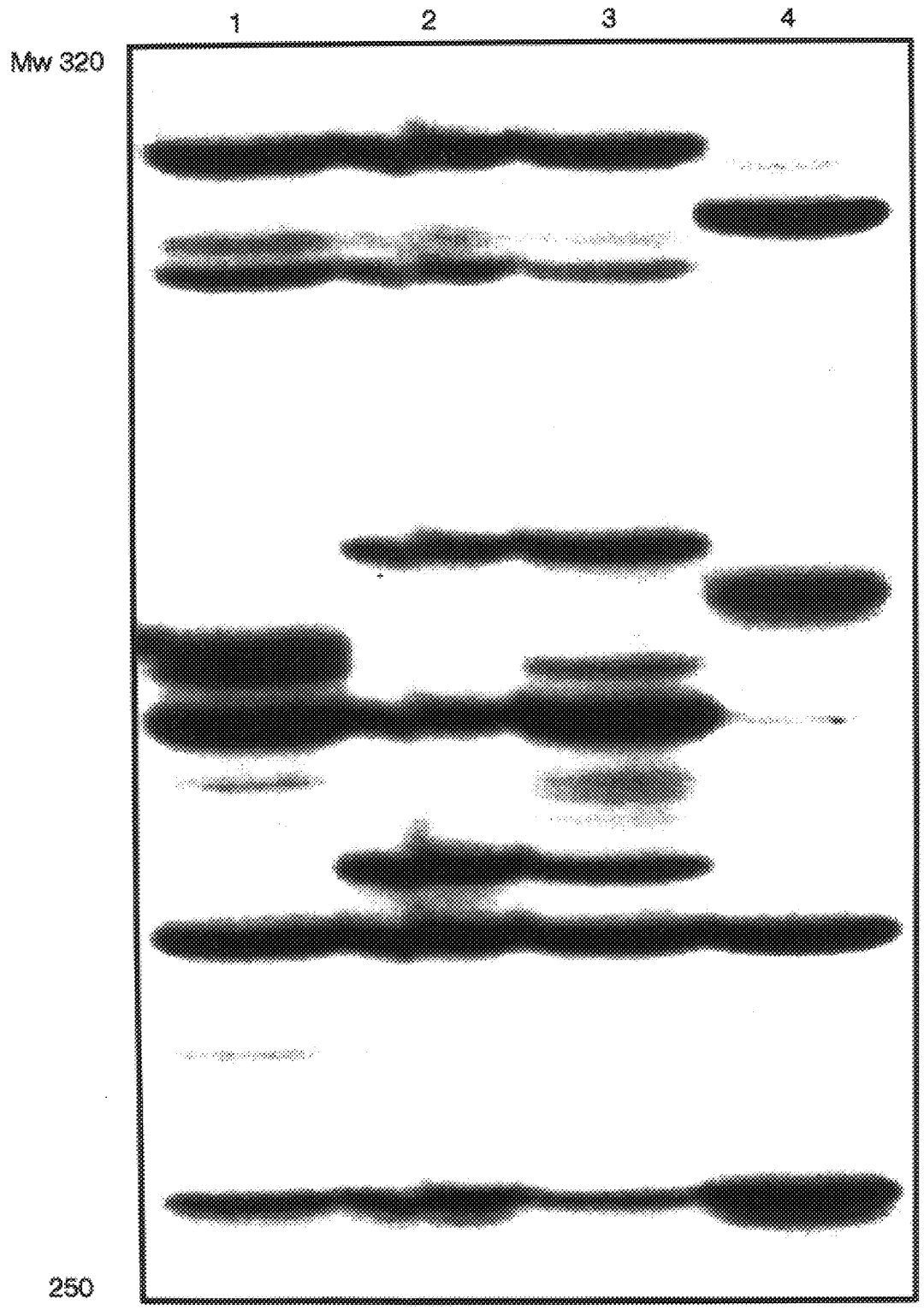
FIG. 4 illustrates the targeting of the (CTT)$_n$ repeat with the restriction enzyme EarI. The figure shows a section of an image, containing products in the range from 250 nucleotides to 320 nucleotides, indicated in the left margin of the figure. The four lanes (1 through 4) show fingerprint patterns that were produced using DNA from 4 independent breeding lines of pepper. Similar patterns will be obtained with other pepper cultivars.

The analysis of amplified products was as described above, except that gel images were obtained using a Fujix BAS2000 phosphorimager. The results are shown in FIG. 4.

Example 3

Targeting of the $(CCTT)_n$ Motif with the Restriction Enzyme EARI

Figure 11:
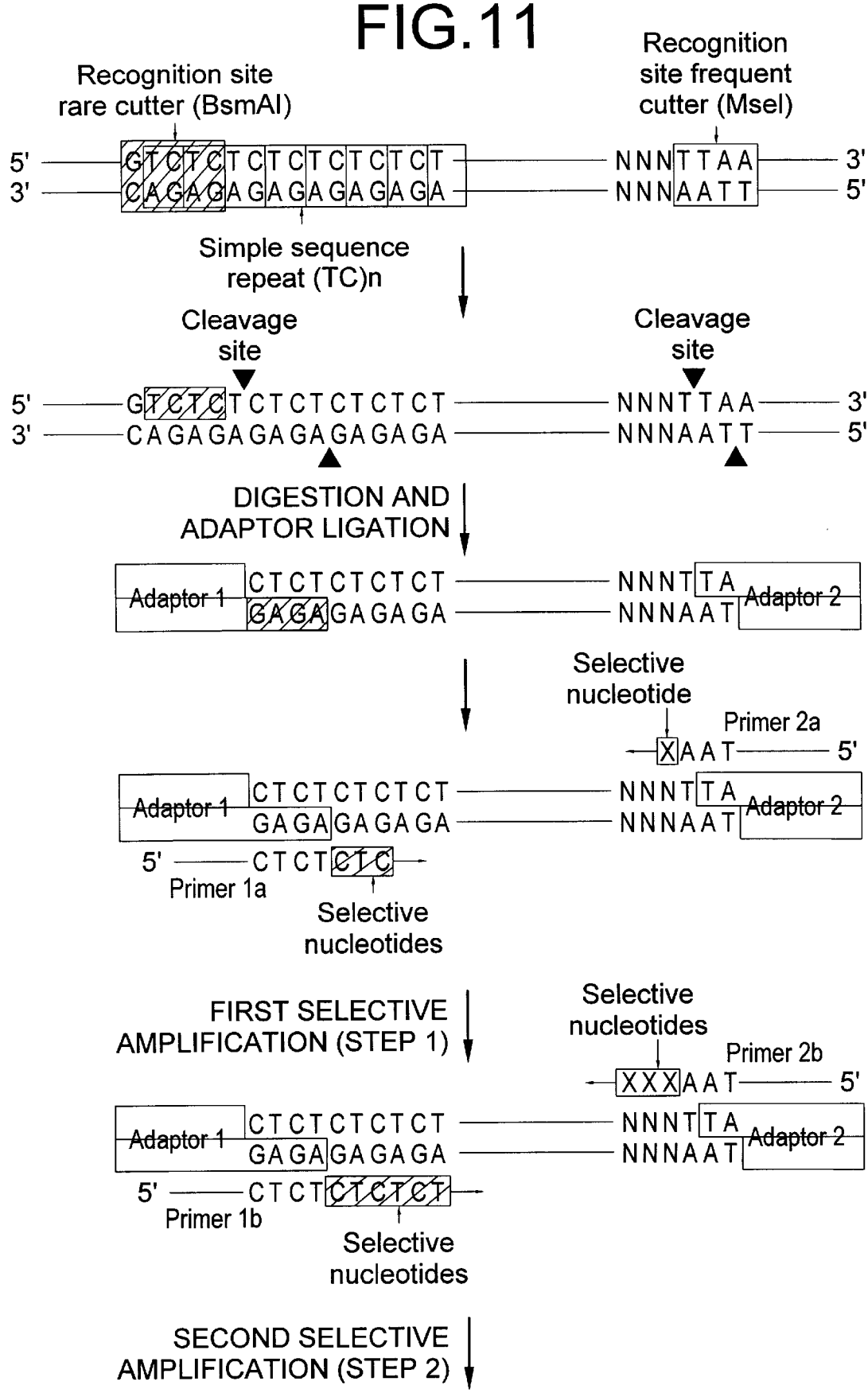
FIG. 11 [SEQ ID NO.: 43–47] provides a graphic outline for the selective amplification of restriction fragments containing simple sequence repeats using a Type 2 restriction enzyme as targeting enzyme such as BsmAI and a frequent cutting enzyme such as MseI. The targeted simple sequence repeat is $(TC)_n$ and the targeting for this repeat is illustrated by small dashed boxes. The selective amplification is performed in two steps.

The restriction enzyme EarI recognizes the sequence [SEQ ID NO.: 19] CT<u>CTTC</u>n'nnn-. For targeting $(CCTT)_n$ motifs a specific form of this recognition sequence, CT<u>CTTC</u>c'ttc- is targeted. This is a third example of a restriction enzyme that cuts outside its recognition sequence, producing an overhang that allows selection in the ligation by using a specific adapter sequence. This strategy is illustrated in FIG. 11. The elements of FIG. 11 corresponding to the rare-cutter, and the adapter- and primer sequences have to be substituted by sequences described here, for example 3.

A) Isolation and modification of the DNA

Figure 5:
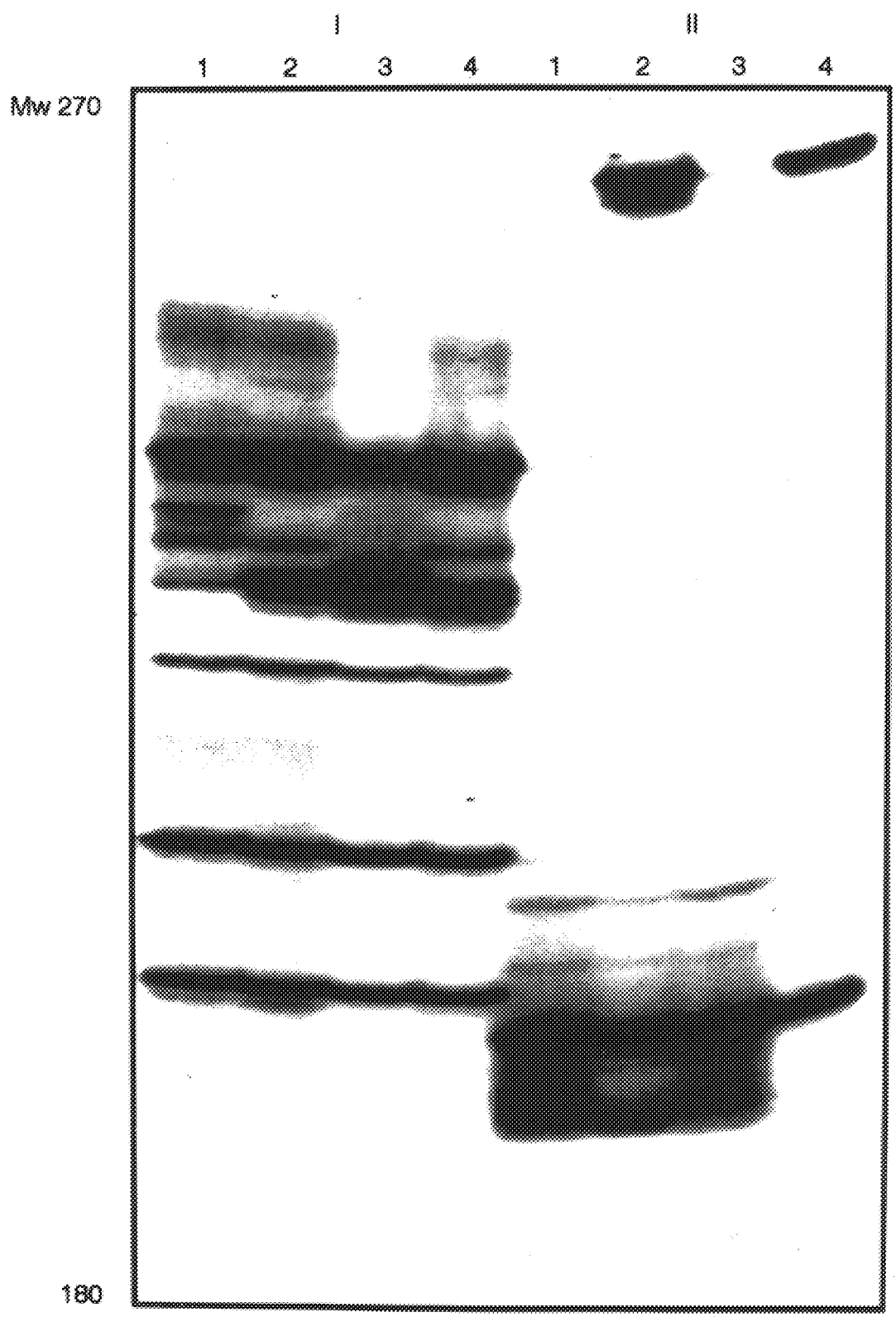
FIG. 5 illustrates the targeting of the $(CCTT)_n$ repeat with the restriction enzyme EarI. The figure shows a section of an image, containing products in the range from 180 nucleotides to 270 nucleotides, indicated on the left. The image contains two panels (I and II, indicated over the image), each containing 4 lanes. In panel I, DNAs were analyzed from 4 individuals from human CEPH families (142403, 142303, 141303 and 88403, in lanes 1, 2, 3 and 4, respectively). Panel II contains patterns from 4 independent chicken from a chicken breeding line (lanes 1, through 4). Similar patterns will be obtained with other chicken breeding lines.

In this example we analyzed both human DNAs and DNA from anonymous chicken. The human DNAs were obtained from CEPH, and originated from the following individuals: 142403, 142303, 141303 and 88403 (FIG. 5, Panel I lane 1 through 4). DNAs from chicken blood were isolated using 10 micro liters frozen blood, following a procedure described by Maniatis et. al., (1982). Patterns obtained with chicken DNAs are displayed in lanes 1 through 4, Panel II.

In case of targeting $(TTCC)_n$ motifs, the bottom strand is specifically designed to target the sequence 5'-TTC present on EarI restriction fragments. The EarI adapter for targeting $(TTCC)_n$ motifs has the following design [SEQ ID NOS.: 5 and 20].

5-biotin-CTCGTAGACTGCGTACC
TCTGACGCATGGAAG-5

Modification of the DNAs was done as described in example 2.

B) Amplification of template DNA

Amplification of products was done using the following primers [SEQ ID NOS.: 21, 16, 22, 18].

Step 1

| EarI primer 1a: | 5-GACTGCGTACCTTCCT | (+2) |
| MseI Primer 2a: | 5-GATGAGTCCTGAGTAAA | (+1) |

Step 2

| EarI primer 1b: | 5-³³P-GACTGCGTACCTTCCTTCC | (+5) |
| MseI primer 2b: | 5-GATGAGTCCTGAGTAAATT | (+3) |

Amplification of products was performed as described in example 1.

C) Analysis of amplified products

The analysis of amplified products was as described above, except that gel images were obtained using a Fujix BAS2000 phosphorimager. The results are shown in FIG. 5.

Example 4

Targeting of the $(TAAA)_n$ Motif with the Restriction Enzyme DRAI

The enzyme DraI recognizes the sequence TT<u>T</u>v·<u>AAA</u>. In this example, a rare-cut restriction enzyme is used that produces a blunt-ended fragment. The strategy is generally explained in FIG. 1. In case of targeting $(TAAA)_n$ motifs, the rare-cutter, adapter- and primer sequences described in FIG. 1 have to be substituted by those described for example 4.

The strategy was tested on DNA from the human family 884 (individuals 1 through 16), made available by CEPH (Centre d'Etude du Polymorphisme Humain, Paris, France).

A) Modification of the DNA

Modification of the DNA was done as described in example 2.

The DraI adapter has the following design [SEQ ID NOS.: 23–24]:

5'-biotin-CTCGTAGACTGCGTACA
CATCTGACGCATGT-5'

Note, that DraI produces blunt ends, thus requiring a blunt-end adapter. Following ligation, biotinylated template molecules are purified as described in example 1.

B) Amplification of template DNA plification was done using the following primers [SEQ ID NOS.: 25–28]:

Step 1

| DraI primer 1a: | 5-GTAGACTGCGTACAAAATAA | (+3) |
| MseI primer 2a: | 5-GATGAGTCCTGAGTAATA | (+2) |

Step 2

| DraI primer 1b: | 5-$^{33}$P-GTAGACTGCGTACAAAATAAATA | (+6) |
| MseI primer 2b: | 5-GATGAGTCCTGAGTAATATC | (+4) |

Amplification of products was performed as described in example 1.

C) Analysis of amplified products

Figure 6:
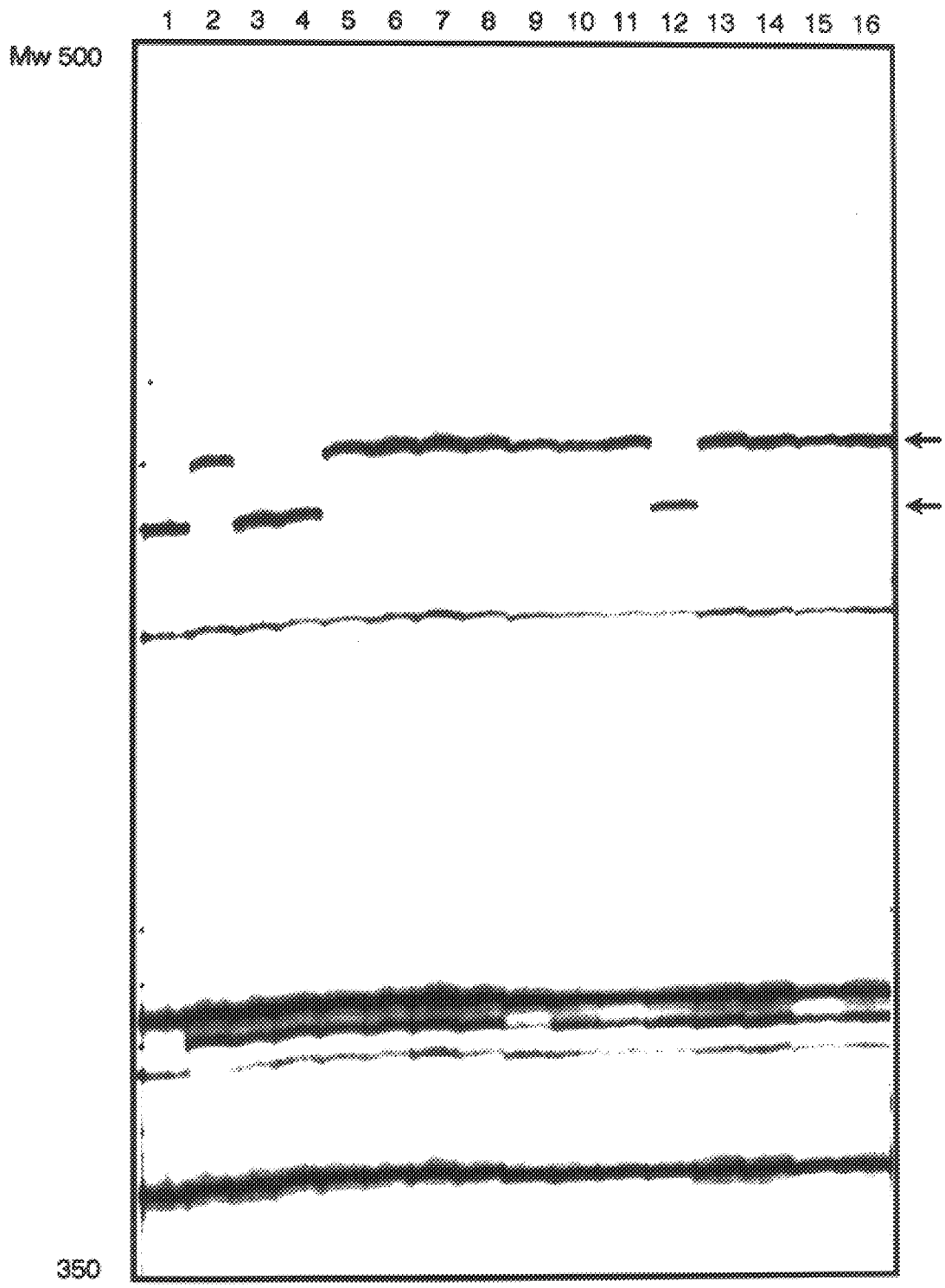
FIG. 6 illustrates the targeting of the $(TAAA)_n$ repeat with the restriction enzyme DraI. The figure displays the electropherogram analyzed on a standard 4.5% polyacrylamide gel. The figure contains fingerprints with products in the range from 350 to 500 nucleotides, indicated on the left of the image. DNAs analyzed in this image were from CEPH family 884, members 1 through 16. Arrow indicate an example of a codominant simple sequence repeat containing marker.

Radiolabelled products from the second amplification reaction were analyzed as described in European Patent Application EP0534858. The products of the reaction are displayed in FIG. 6.

Example 5

Targeting of the (TG)$_n$ Motif with the Restriction Enzyme NLAIII

Figure 10:
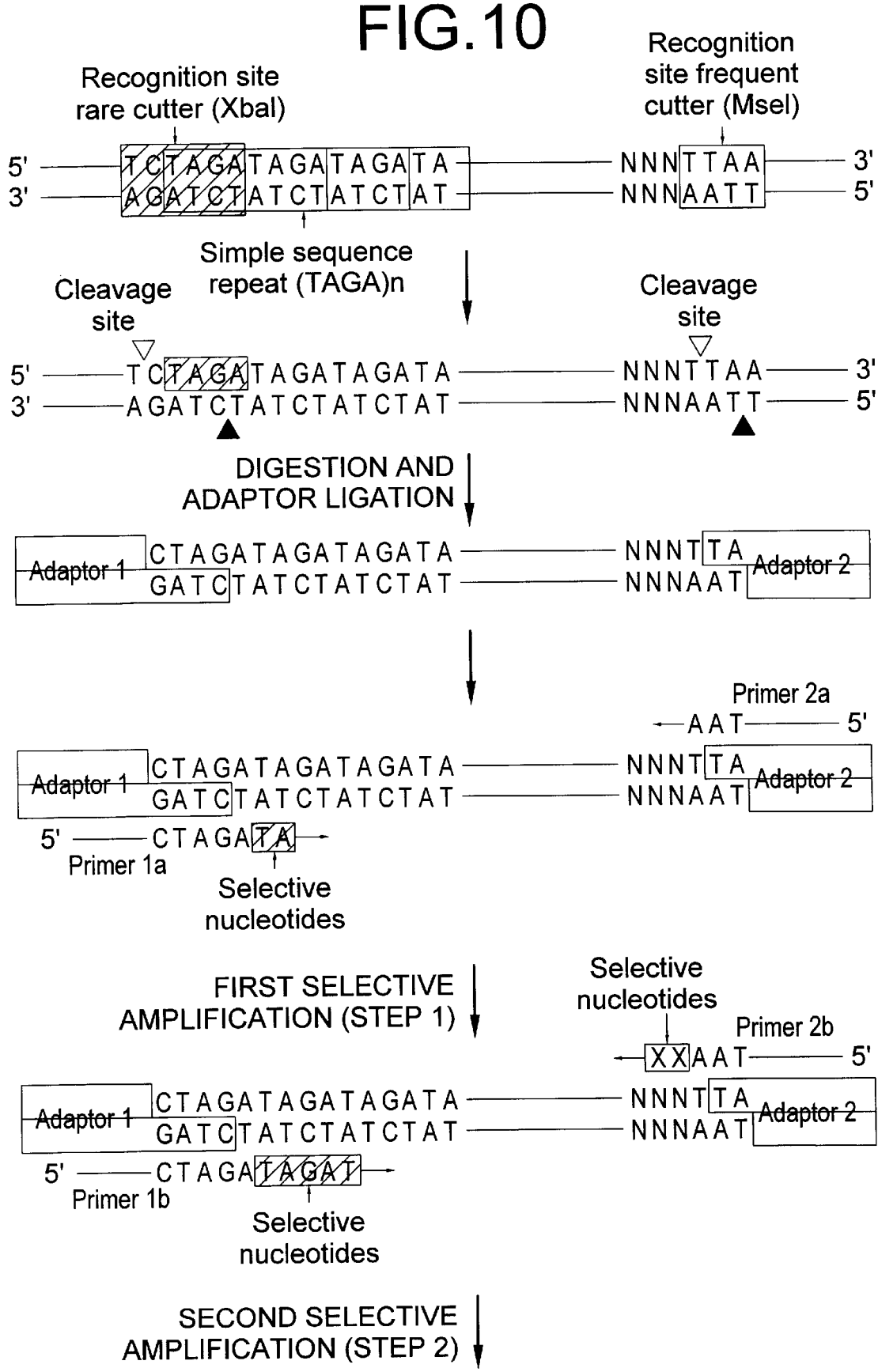
FIG. 10 [SEQ ID NOS.: 39–42] provides a graphic outline for the selective amplification of restriction fragments containing simple sequence repeats using a Type 1 restriction enzyme as targeting enzyme such as XbaI and a frequent cutting enzyme such as MseI. The targeted simple sequence repeat is $(TAGA)_n$ and the targeting for this repeat is illustrated by small dashed boxes. The selective amplification is performed in two steps.

The enzyme NlaIII recognizes the sequence ˙CA<u>TG</u>$^\vee$. In this example, a restriction enzyme is used that produces a staggered ended fragment. This strategy is explained in detail in FIG. 10. In case of targeting (TG)$_n$ motifs, the elements of FIG. 10 corresponding to the rare-cutter, and the adapter- and primer sequences have to be substituted by sequences described here, for example 5.

The strategy was tested on DNA from anonymous lines of cucumber. DNA was isolated as described in example 1.

A) Modification of the DNA

Modification of the DNA was done as described in example 2.

The NlaIII adapter has the following design [SEQ ID NOS.: 29–30]:

| 5-biotin-CTCGTAGACTGCGTACCCATG |
| TCTGACGCATGG-5 |

Template molecules were purified as described in example 1.

B) Amplification of template DNA

Amplification was done using the following primers [SEQ ID NOS.: 31–33 and 18]:

Step 1

| NlaIII primer 1a: | 5-CTGCGTACCCATGTGT | (+3) |
| MseI primer 2a: | 5-GATGAGTCCTGAGTAAA | (+1) |

Step 2

| NlaIII primer 1b: | 5-$^{33}$P-GCGTACCCATGTGTGTG | (+6) |
| MseI primer 2b: | 5-GATGAGTCCTGAGTAAATT | (+3) |

Amplification of products was performed as described in example 1.

C) Analysis of amplified products

Figure 7:
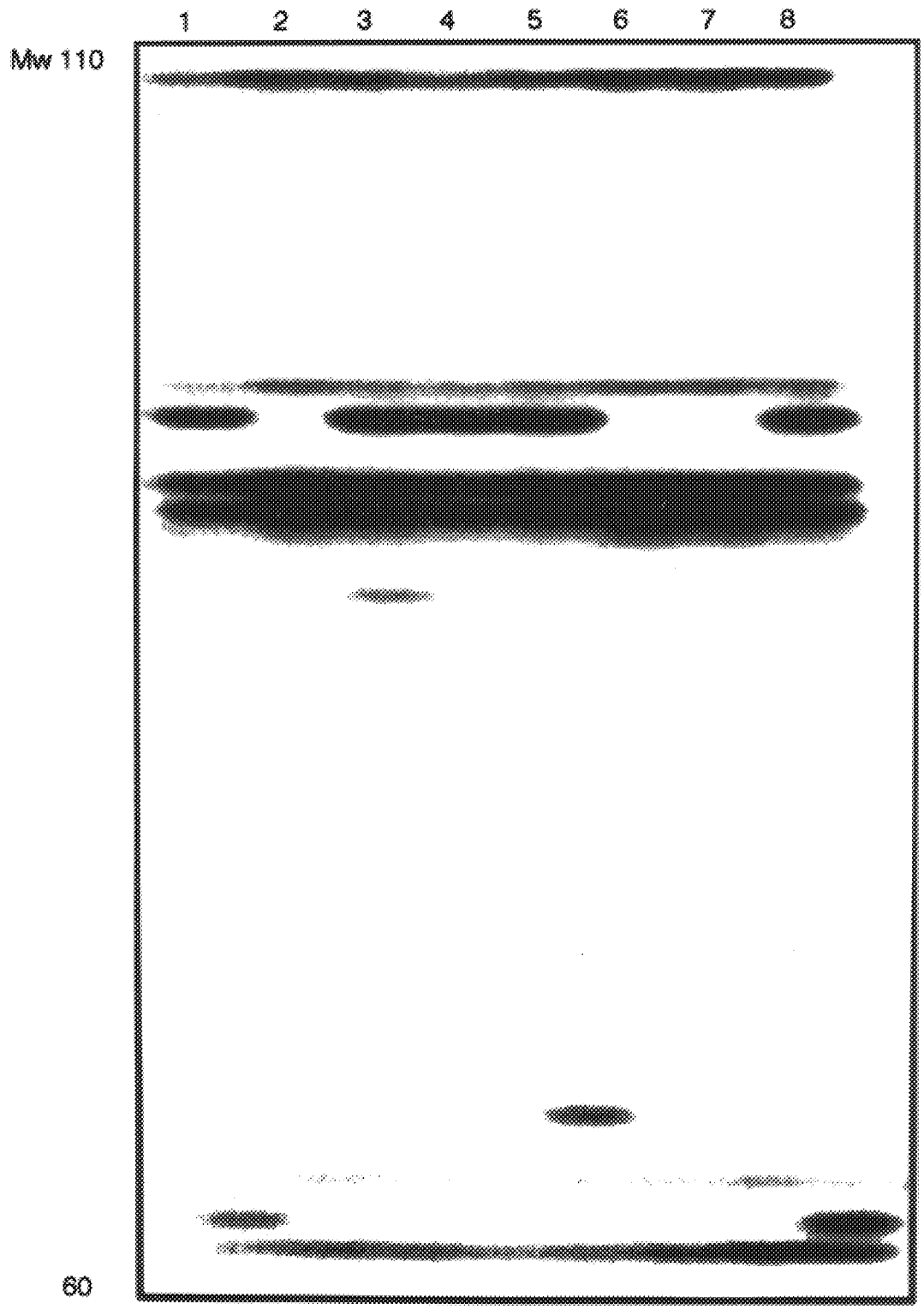
FIG. 7 illustrates the targeting of the $(TG)_n$ repeat with the restriction enzyme NlaIII. The figure shows a section of an image, containing products in the range from 60 nucleotides to 110 nucleotides, indicated on the left. The image contains 8 lanes, with fingerprinting patterns from 8 anonymous cucumber breeding lines. Similar patterns will be obtained with other cucumber breeding lines.

The analysis of amplified products was as described above, except that gel images were obtained using a Fujix BAS2000 phosphorimager. The results are shown in FIG. 7.

Example 6

Targeting of (TAGA)$_n$ Motifs with the Restriction Enzyme XBAI

The restriction enzyme XbaI recognizes the sequence T$^\vee$C TAG˙A. In this example, a restriction enzyme is used that produces a staggered ended fragment. This strategy is explained in detail in FIG. 10.

The strategy was tested on DNA from anonymous lines of Tomato. DNA was isolated as described in example 2.

A) Modification of the DNA

Modification of the DNA was done as described above in example 2.

The XbaI adapter has the following design [SEQ ID NOS.: 26 and 34]:

| 5-biotin-CTCGTAGACTGCGTACA |
| TCTGACGCATGTGATC-5 |

Template molecules were purified as described in example 1.

B) Amplification of template DNA

Amplification was done using the following primers [SEQ ID NOS.: 35–38]:

Step 1

| XbaI primer 1a: | 5-CTGCGTACACTAGATA | (+2) |
| MseI primer 2a: | 5-GATGAGTCCTGAGTAA | (+0) |

Step 2

| XbaI primer 1b: | 5-$^{33}$P-GCGTACACTAGATAGAT | (+5) |
| MseI primer 2b: | 5-GATGAGTCCTGAGTAACT | (+2) |

Amplification of products was performed as described in example 1.

C) Analysis of amplified products

Figure 8:
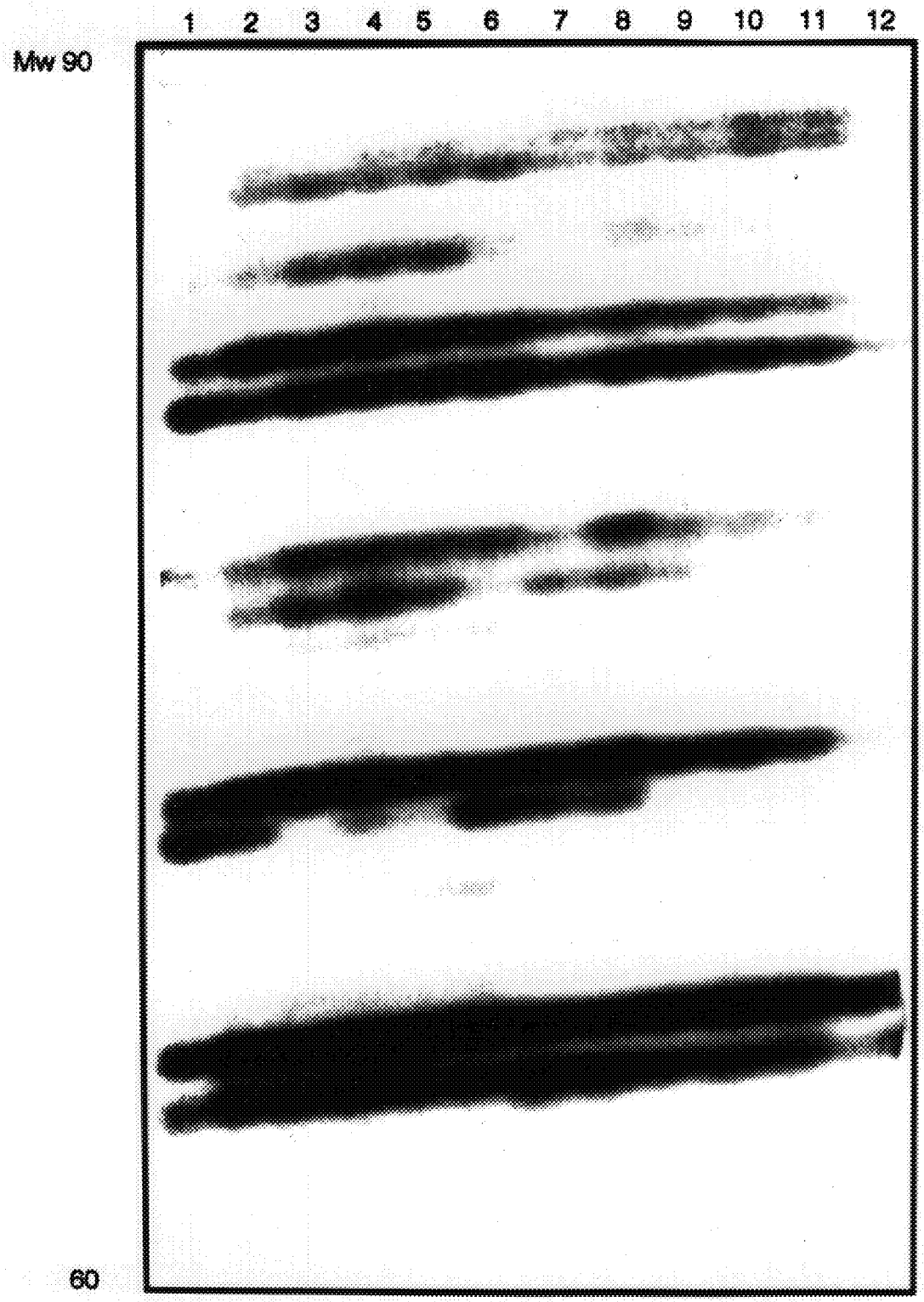
FIG. 8 illustrates the targeting of the $(TAGA)_n$ repeat with the restriction enzyme XbaI. The figure shows a section of an image, containing products in the range from 60 nucleotides to 90 nucleotides, indicated on the left. The image contains 12 lanes, with fingerprinting patterns from 12 anonymous tomato breeding lines. Similar patterns will be obtained with other tomato breeding lines.
Figure 9:
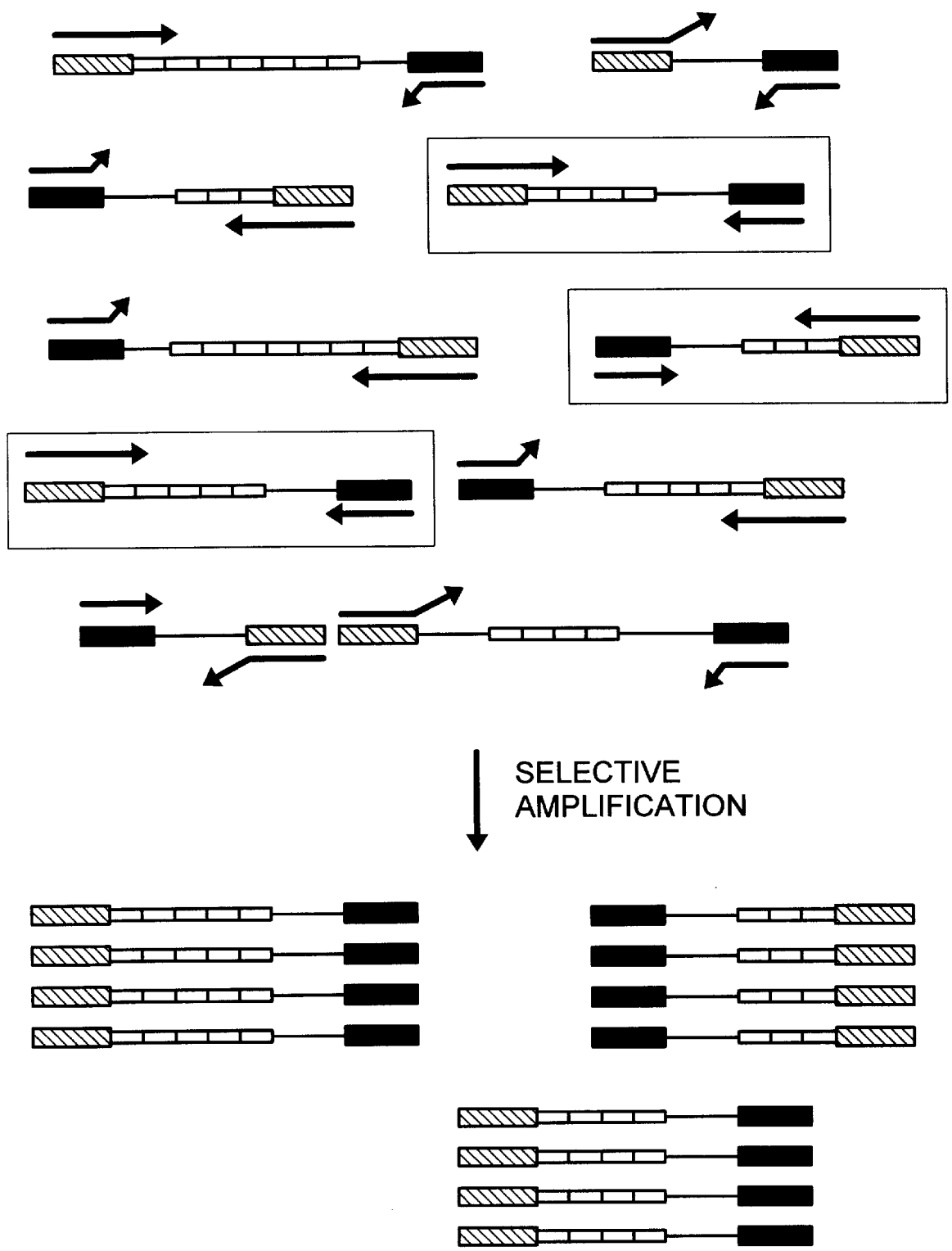
FIG. 9 provides a schematic outline of the selective amplification of restriction fragments comprising a simple sequence repeat. The shaded boxes represent the adaptor and—part of—the recognition site of the targeting restriction enzyme, the filled boxes represent the adaptor and—part of—the recognition site of the frequent cutting restriction enzyme, the hollow boxes represent the simple sequence repeat units and the lines represent the nucleic acid sequence flanking the simple sequence repeat. The long arrows represent the matching and non-matching selective primers one and the short arrows represent the matching and non-matching selective primers two. Only those restriction fragments to which both primers match with the ends will be amplified exponentially.

The analysis of amplified products was as described in example 1, except that gel images were obtained using a Fujix BAS2000 phosphorimager. The results are shown in FIG. 8. FIG. 8 shows a section of an image, containing products in the range from 60 nucleotides to 90 nucleotides, indicated on the left. The image contains 12 lanes, with fingerprinting patterns from 12 anonymous tomato breeding lines. Similar patterns will be obtained with other tomato breeding lines.

We claim:

1. Process for the selective amplification of restriction fragments comprising simple sequence repeats, comprising the following:

(a) digesting a starting target DNA with two or more different restriction enzymes, at least one of these enzymes cleaving at or near its recognition nucleotide sequence overlapping or flanking with the simple sequence repeat (referred to as first restriction enzyme) and at least one of these enzymes cleaving the restriction fragments into amplificable restriction fragments (referred to as second restriction enzyme) to obtain restriction fragments, (b) ligating an appropriate double stranded oligonucleotide adaptor to each of the ends of the restriction fragments produced by said restriction enzymes, (c) amplifying the restriction fragments of step b) using two or more different amplification primers with the following general structure:
one primer having a sequence at its 5' end matching the common sequence of the restriction fragments produced with the first restriction enzyme, and a sequence at its 3' end of at least 5 nucleotides matching the sequence of the simple sequence repeat (referred to as primer one);
one primer having a sequence at its 5' end matching the common sequence of the restriction fragments produced with the second restriction enzyme (referred to as primer two), (d) recovering the amplified fragments.

2. Process for the selective amplification of restriction fragments according to claim 1 wherein the two or more different amplification primers have the following general design:
one primer having a sequence at its 5' end matching the sequence of the adaptor of the first restriction enzyme and its recognition site, and a sequence at its 3' end of at least 5 nucleotides matching the sequence of the simple sequence repeat (referred to as primer one);
one primer having a sequence at its 5' end matching the sequence of the adaptor of the second restriction enzyme and its recognition sequence, and a sequence at its 3' end ranging from 0 to 4 randomly chosen nucleotides (referred to as primer two).

3. Process according to claim 1 wherein said first restriction enzyme has a recognition sequence which comprises at least one nucleotide which does not overlap with the simple sequence repeat.

4. Process according to claim 1 wherein said first restriction enzyme has a recognition sequence which is located immediately adjacent to the simple sequence repeat.

5. Process according to claim 1 wherein said restriction fragments are amplified in two or more consecutive amplification steps, whereby (i) in the first amplification step, two different PCR primers are used with the following general design:
primer one having a sequence at its 5' end matching the common sequence of the restriction fragments produced with the first restriction enzyme and a sequence at its 3' end ranging from 0 to 3 nucleotides, matching the sequence of the simple sequence repeat;
primer two having a sequence at its 5' end matching the common sequence of the restriction fragments produced with the second restriction enzyme and a sequence at its 3' end ranging from 0 to 3 randomly chosen nucleotides;

(ii) in each following amplification step two different PCR primers are used, whereby
primer one has the same nucleotide sequence as primer one in the first amplification step and a sequence at its 3' end of at least one additional nucleotide matching the sequence of the simple sequence repeat;
primer two is identical to primer two in the first amplification step or has the same nucleotide sequence as primer two in the first amplification step and a sequence at its 3' end of at least one additional randomly chosen nucleotide.

6. Process according to claim 1 wherein said first restriction enzyme is a type 2 restriction enzyme and wherein said primer one has a sequence at its 5' end matching the sequence of the adaptor of the first restriction enzyme, and a sequence at its 3' end of at least 5 nucleotides matching the sequence of the simple sequence repeat.

7. Process according to claim 1 wherein said starting DNA is genomic DNA.

8. Process according to claim 7 wherein said genomic DNA is from eukaryotic organisms.

9. Process according to claim 1 wherein the amplified fragments are recovered as DNA fingerprints.

10. Process for identifying the differences or similarities, between different target DNAs, said process comprising comparing the DNA fingerprints from each of said target DNAs obtained according to claim 9, and identifying the differences or similarities between the DNA fingerprints between the different target DNAs.

11. Process according to claim 1 wherein one of the restriction enzymes cleaves a four-base sequence.

12. Process according to claim 1 wherein primer two has a sequence at the 5' end matching part of the common sequence of the restriction fragments produced with the second restriction enzyme.

13. Process according to claim 1 wherein primer two further comprises at least one randomly chosen nucleotide at its 3' end.

14. Process according to claim 13 wherein primer two comprises a sequence at its 3' end of 1, 2, 3 or 4 randomly chosen nucleotides.

15. Process according to claim 8 wherein said eukaryotic organisms are selected from the group consisting of animals, plants and humans.

* * * * *